US006322988B1

(12) United States Patent
Dawson et al.

(10) Patent No.: US 6,322,988 B1
(45) Date of Patent: Nov. 27, 2001

(54) METHOD FOR DETERMINING POLYNUCLEOTIDE SEQUENCE VARIATIONS

(75) Inventors: Elliott P. Dawson, Murfreesboro; John A. Phillips, III, Brentwood, both of TN (US)

(73) Assignees: BioVentures, Inc., Murfreesboro; Vanderbilt University, Nashville, both of TN (US)

( * ) Notice: Subject to any disclaimer, the term of this patent is extended or adjusted under 35 U.S.C. 154(b) by 0 days.

(21) Appl. No.: 09/719,130

(22) PCT Filed: Aug. 19, 1999

(86) PCT No.: PCT/US99/18965

§ 371 Date: Dec. 8, 2000

§ 102(e) Date: Dec. 8, 2000

(87) PCT Pub. No.: WO00/11221

PCT Pub. Date: Mar. 2, 2000

Related U.S. Application Data

(60) Provisional application No. 60/097,136, filed on Aug. 19, 1998.

(51) Int. Cl.$^7$ .............................. C12Q 1/68; C12P 19/34; C07H 19/00
(52) U.S. Cl. .............................. 435/6; 435/91.2; 536/22.1
(58) Field of Search ........................ 435/6, 91.2; 536/22.1

(56) References Cited

U.S. PATENT DOCUMENTS

| 5,683,869 | 11/1997 | Shaw et al. ............................... 435/6 |
| 5,847,162 | * 12/1998 | Lee et al. .............................. 536/22.1 |
| 5,891,628 | 4/1999 | Reeders et al. ........................... 435/6 |
| 5,928,906 | 7/1999 | Köster et al. ......................... 435/91.2 |

OTHER PUBLICATIONS

Iwahana H, Yoshimoto K, Mizusawa N, Kudo E and Itakura M. Multiple fluorescence–based PCR–SSCP analysis. Biotechniques, 16(2): 296–305, 1994.*

Iwahana H, Fujimura M, Takahashi Y, Iwabuchi T, Yoshimoto K and Itakura M. Multiple flurescence–based PCR–SSCP analysis using internal fluorescent labeling of PCR products. Biotechniques, 21(3): 510–519, 1996.*

Dicker AP et al. Sequence analysis of a human gene responsible for drug resistance: a rapid method for manual and automated direct sequencing of products generated by polymerase chain reaction. Biotechniques, 7(8): 830–837, 1989.*

Dicker, Adam P. et al., "Sequence Analysis of a Human Gene Responsible for Drug Resistance: A Rapid Method for Manual and Automated Direct Sequencing of Products Generated by the Polymerase Chain Reaction," *BioTechniques*, 7(8):830–837 (1989).

Molecular and Cell Biology Catalog 1993, *Pharmacia*, pp. 115–132.

Plaschke, J. et al., "Doublex Sequencing in Molecular Diagnosis of Hereditary Diseases," *BioTechniques*, 24(5):838–841 (May 1998).

Rao, Venigalla B., "Direct Sequencing of Polymerase Chain Reaction–Amplified DNA," *Analytical Biochemistry*, 216:1–14 (1994).

Voss, H. et al., "Automated Cycle Sequencing with Taquenase™: Protocols for Internal Labeling, Dye Primer and Doublex' Simultaneous Sequencing," *BioTechniques*, 23(2):312–318 (Aug. 1997).

Wiemann, Stefan et al., "Simultaneous On–Line DNA Sequencing on Both Strands with Two Fluorescent Dyes," *Analytical Biochemistry*, 224:117–121 (1995).

* cited by examiner

*Primary Examiner*—Eggerton A. Campbell
*Assistant Examiner*—Suryaprabha Chunduru
(74) *Attorney, Agent, or Firm*—David A. Farah, M.D.; Sheldon & Mak

(57) ABSTRACT

A method of determining the presence and identity of a variation in a nucleotide sequence between a first polynucleotide and a second polynucleotide comprising, first, providing a sample of the first polynucleotide and selecting a region of the first polynucleotide potentially containing the variation. Then, the selected region is subjected to a template producing amplification reaction to produce a plurality of double stranded polynucleotide templates which include the selected region. Next, a family of labeled, linear polynucleotide fragments is produced from both strands of the template simultaneously by a fragment producing reaction using a set of primers. Then, the location and identity of at least some of the bases in the selected region of the first polynucleotide is determined using the labels present in the fragments. Next, the location and identity of the bases determined is compared with the location and identity of bases from a second polynucleotide, thereby identifying the presence and identity of a variation in a nucleotide sequence between the selected region of the first polynucleotide and a corresponding region of the second polynucleotide.

66 Claims, No Drawings

ND FOR DETERMINING
METHOD FOR DETERMINING POLYNUCLEOTIDE SEQUENCE VARIATIONS

This application is a 371 of PCT/US99/18965 filed Aug. 19, 1999, which claims benefit to Provisional Application 60/097,136 filed Aug. 19, 1998.

BACKGROUND

Individual DNA sequence variations in the human genome are known to directly cause specific diseases or conditions, or to predispose certain individuals to specific diseases or conditions. Such variations also modulate the severity or progression of many diseases. Additionally, DNA sequence variations between populations. Therefore, determining DNA sequence variations in the human genome is useful for making accurate diagnoses, for finding suitable therapies, and for understanding the relationship between genome variations and environmental factors in the pathogenesis of diseases and prevalence of conditions.

There are several types of DNA sequence variations in the human genome. These variations include insertions, deletions and copy number differences of repeated sequences. The most common DNA sequence variations in the human genome, however, are single base pair substitutions. These are referred to as single nucleotide polymorphisms (SNPs) when the variant allele has a population frequency of at least 1%.

SNPs are particularly useful in studying the relationship between DNA sequence variations and human diseases and conditions because SNPs are stable, occur frequently and have lower mutation rates than other genome variations such as repeating sequences. In addition, methods for detecting SNPs are more amenable to being automated and used for large-scale studies than methods for detecting other, less common DNA sequence variations.

A number of methods have been developed which can locate or identify SNPs. These methods include dideoxy fingerprinting (ddF), fluorescently labeled ddF, denaturation fingerprinting (DnF1R and DnF2R), single-stranded conformation polymorphism analysis, denaturing gradient gel electrophoresis, heteroduplex analysis, RNase cleavage, chemical cleavage, hybridization sequencing using arrays and direct DNA sequencing.

The known methods for locating or identifying SNPs are associated with certain disadvantages. For example, some known methods do not identify the specific base changes or the precise location of these base changes within a sequence. Other known methods are not amenable to analyzing many samples simultaneously or to analyzing pooled samples. Still other known methods require different analytical conditions for the detection of each variation. Additionally, some known methods cannot be used to quantify known SNPs in genotyping assays. Further, many known methods have excessive limitations in throughput.

Thus, there is a need for a new method to determine the presence and identity of a variation in a nucleotide sequence between a first polynucleotide and a second polynucleotide, including the presence of an SNP in the genome of a human individual. Preferably, the method could determine the presence and identity of a variation in a nucleotide sequence between a first polynucleotide and a second polynucleotide in a pooled sample. Additionally preferably, the method could determine whether two or more variations reside on the same or different alleles in an individual, and could be used to determine the frequency of occurrence of the variation in a population. Further preferably, the method could screen large numbers of samples at a time with a high degree of accuracy.

SUMMARY

In one embodiment, there is provided a method of determining the presence and identity of a variation in a nucleotide sequence between a first polynucleotide and a second polynucleotide. The method comprises, first, providing a sample of the first polynucleotide and selecting a region of the first polynucleotide potentially containing the variation. Then, the selected region is subjected to a template producing amplification reaction to produce a plurality of double stranded polynucleotide templates which include the selected region. Next, a family of labeled, linear polynucleotide fragments is produced from both strands of the template simultaneously by a fragment producing reaction using a set of primers. Each of the family of fragments is terminated by a terminator at the 3' end of the fragment. The family of fragments includes at least one fragment terminating at each possible base, represented by the terminator, of that portion of both template strands flanked by the primers. Then, the locations and identities of at least some of the bases in the selected region of the first polynucleotide are determined using the labels present in the fragments. Next, the location and identity of the bases determined is compared with the location and identity of bases from a second polynucleotide, thereby identifying the presence and identity of a variation in a nucleotide sequence between the selected region of the first polynucleotide and a corresponding region of the second polynucleotide.

DESCRIPTION

The present invention includes a method for determining the presence, location or identity, or a combination of these, of one or more polynucleotide sequence differences between at least two polynucleotides. Among other uses, the present method can locate and identify single nucleotide polymorphisms present in the human genome. Further, the present method can discover previously unidentified genome variations between individuals, between an individual and a population, and between populations. Also, the present method can determine the frequency or distribution of genome variations within populations. Additionally, the present method can relate specific genome variations found in a population to specific phenotypes within that population. Still further, the present method can determine the allelic distribution of genome variations in individuals and populations.

More specifically, the present method of the present invention can provide the following types of information on polynucleotide sequence variation between two polynucleotides. First, the present method can identify the position of all the nucleotides in a selected region of a first polynucleotide that are different from one or more additional polynucleotides. Second, the present method can identify which nucleotide has replaced another nucleotide in a polynucleotide. Third, the present method can determine the proportion of the polynucleotide molecules that have each of the nucleotide changes that can occur at a given location in the sequence. Fourth, where two different polynucleotides have a plurality of nucleotide differences, the present method can provide information on which differences occur together.

The present method has several combined advantages over known methods. Generally, the present method provides more types of information, is more widely applicable and is simpler to perform. Particularly advantageous, the present method is a single technology that can simultaneously identify and quantitate known and unknown variations and determine the locations, identities and frequencies of all variations between two populations of polynucleotides. Additionally, the present method can determine whether two or more genetic variations reside on the same or different alleles in an individual, and can be used to determine the frequency of occurrence of the variation in a population.

Further, the present method can be used on any type of polynucleotide, from any source. In addition to determining the location and identity of SNPs, the present method can be used to determine the presence and type of polynucleotide variations including substitutions, deletions, insertions, expansions and contractions involving multiple nucleotides, and truncated or chimeric molecules. Further, the present method can identify alterations in the relative copy number of sequences in diploid organisms that involve the loss of one copy of a polynucleotide such as loss of heterozygosity, or that involve the gain of additional copies of a polynucleotide such as conditions in which extra copies of chromosomes are present.

Additionally, in population studies, the present method can be used to determine the frequencies of each polynucleotide variation by analysis of a single pooled sample that is composed of samples taken from multiple individuals. Finally, the present method can be used to estimate the proportion of the population that is susceptible or resistant to a factor that is dependant on the presence or absence of a particular polynucleotide variation or to detect polynucleotide variations in populations that occur over time, such as in cultures of pooled bacteria. Also, the present method can be automated.

The present method preferably comprises providing a sample of a first polynucleotide. Then, one or more specific regions of the first polynucleotide are selected where the presence, location or identity of at least one sequence variation is to be determined. Next, the selected region is subjected to a template producing amplification reaction. In a preferred embodiment, the templates produced are purified to remove other amplification reaction components.

Then, a family of labeled, linear polynucleotide fragments is produced from both strands of the template simultaneously by a fragment producing reaction using a set of primers. The family of fragments produced by this reaction includes fragments which terminate by a dideoxyterminator at the 3' end at each possible base, represented by the dideoxyterminator, of both templates strands flanked by the primers.

Finally, the location and identity of each base in the selected region of the template from the first polynucleotide are identified using the labels present in the fragments. The location and identity are compared to a known reference sequence, or are compared with corresponding information determined from a family of labeled, linear polynucleotide fragments produced from a second polynucleotide using the present method. The comparison yields information about the presence, location or identity of one or more sequence differences between the first polynucleotide and the reference sequence, or between the first polynucleotide and the second polynucleotide. The present method will now be discussed in greater detail.

1) Provision of Sample Polynucleotide:

Before template amplification, the polynucleotide or polynucleotides of interest must be obtained in suitable quantity and quality for the chosen amplification method to be used. Some suitable samples can be purchased from suppliers such as the American Type Culture Collection, Manassas, Va., US or Coriell Institute for Medical Research, Camden, N.J., US. Additionally, commercially available kits for obtaining suitable polynucleotide samples from various sources are available from Qiagen Inc., Chatsworth, Calif., US; Invitrogen Corporation, Carlsbad, Calif., US; and 5'-3' Prime Inc., Boulder, Colo., US, among other suppliers. Further, general methods for obtaining polynucleotides from various sources for amplification methods including PCR and RT-PCR are well known to those with skill in the art.

Advantageously, the present method allows for simultaneous analysis of polynucleotides obtained from a plurality of samples. If two or more polynucleotide samples are pooled prior to analysis, then the polynucleotide samples are preferably mixed in equal proportions.

2) Selection of One or More Regions of the Polynucleotide for Analysis:

Next, one or more specific regions of a first polynucleotide are selected where the presence, location or identity of at least one sequence variation is to be determined. As used in this disclosure, "region" should be understood to include a plurality of discontinuous sequences on the same polynucleotide. Region selection can be based upon known sequence information for the same or related polynucleotides, or can be based upon the region of interest of a reference polynucleotide which is sequenced using techniques well known to those with skill in the art.

3) Amplification of the Selected Region:

Once the region is selected, the region is subjected to an amplification reaction according to techniques known to those with skill in the art, to produce templates. As used in this disclosure, "template" or "templates" should be understood to include a plurality of templates produced from discontinuous sequences on the same polynucleotide. In a preferred embodiment, the templates produced by this amplification reaction comprise double stranded nucleic acid strands of between about 50 and 50,000 nucleotides per strand. In a particularly preferred embodiment, the amplification method is PCR where the polynucleotide being analyzed is DNA, or is RT-PCR where the polynucleotide being analyzed is RNA, though the templates can be produced by any suitable amplification method for the polynucleotide being analyzed as will be understood by those with skill in the art with reference to this disclosure. Suitable kits for performing PCR and RT-PCR are available from a number of commercial suppliers, including Amersham Pharmacia Biotech, Inc., Piscataway, N.J., US; Invitrogen Corporation, Carlsbad, Calif., US; Life Technologies, Inc., Gaithersburg, Md., US; and Perkin-Elmer, Corp., Norwalk, Conn., US, among other sources.

4) Template Purification:

In a preferred embodiment, the templates produced by the amplification reaction are purified from other amplification reaction components according to techniques known to those with skill in the art. For example, the amplification reaction mixture can be subjected to polyacrylamide gel electrophoresis or agarose gel electrophoresis, and templates having the expected size are purified from the other amplification reaction components by ethanol or isopropanol precipitation, membrane purification or column purification. After purification, the templates should be kept in solution, preferably in sterile, nuclease free, 18 megaohm water or in 0.1×TE.

5) Production of a Family of Labeled, Linear Polynucleotide Fragments:

The templates produced by amplification are then used to produce a family of labeled, linear polynucleotide fragments from both strands of each template simultaneously by a fragment producing reaction using a set of primers. The fragment producing reaction is similar to an amplification reaction except that the polynucleotide fragments amplified comprise a family of fragments from both template strands flanked by the primers, and the family of fragments terminate by a dideoxyterminator at the 3' end, and terminate at each possible base corresponding to a dideoxyterminator, rather than a single polynucleotide sequence spanning the full length of the template strands flanked by the primers.

In a preferred embodiment, the fragment producing reaction is performed as follows, though other equivalent procedures will also be suitable as will be understood by those with skill in the art with reference to this disclosure. First, a region of the polynucleotide sequence lying within the template is selected for analysis. Next, a pair of primers is synthesized that flanks the selected region. In a preferred embodiment, the polynucleotide length between the forward and reverse primer pair from their respective 3' ends is between about 50 and 2000 nucleotides in length. In a particularly preferred embodiment, the polynucleotide length between the forward and reverse primer pair from their respective 3' ends is between about 100 and 1000 nucleotides in length.

Then, a reaction mixture is made comprising the template, the primer pair, a solvent, a set of four 2'deoxynucleotide triphosphates (dNTPs), a pair of 2'–3'-dideoxynucleotide triphosphates (ddNTPs), buffer, a divalent cation, DNA dependant DNA polymerase and at least one detectible labeling agent. This reaction mixture is added to a suitable reaction vessel, such as 0.2 ml or 0.5 ml tubes or in the wells of a 96-well thermocycling reaction plate. Using this method, multiple polynucleotides can be analyzed simultaneously in the same physical location either by having pooled sample in the original template producing amplification reaction, or by pooling templates produced by the template producing amplification reactions. When multiple polynucleotides are being simultaneously analyzed by either option, the reaction mixture includes templates that are specific for each polynucleotide. Obviously, however, two polynucleotides can also be analyzed in separate physical locations simultaneously, to save time. Each reaction is then overlaid with an evaporation barrier, such as mineral oil or paraffin wax beads, and the reaction mixtures are cycled over suitable temperature ranges for suitable times.

The reaction mixture more specifically comprises between about 1 pg and 200 ng, and more preferably between 100 and 150 ng, of the template placed in a volume of solvent comprising between about 1 and 3 $\mu$l of sterile, nuclease free, 18 megaohm water or 0.1×TE buffer. The synthesized primer pair is added to this reaction mixture in a final concentration of between about 1 and 50 pMoles per reaction for a total reaction volume of about 20 $\mu$l.

The reaction mixture further comprises approximately equal concentrations of the four dNTPs: dATP, dCTP, dGTP and dTTP. However, dUTP can advantageously be used in place of dTTP to improve results, such as when there are more than five contiguous thymine residues in the template to be analyzed. Each dNTP preferably has a concentration of between about 1 $\mu$molar and 1 mmolar. In a preferred embodiment, the concentration of each of the four dNTPs is between about 20 and 200 $\mu$molar.

The reaction mixture additionally comprises two non-Watson-Crick-pairing bases of the set of 2'–3'dideoxynucleotide triphosphates (ddNTP) consisting of ddATP, ddCTP, ddGTP and ddTTP (or ddUTP in place of ddTTP). Suitable pairs include ddATP:ddCTP, ddATP:ddGTP, ddCTP:ddTTP, ddGTP:ddTTP. Preferably, one of the two ddNTPs must be a pyrimidine nucleotide and the other must be a purine nucleotide. In a particularly preferred embodiment, the ddNTPs pair is either ddATP:ddCTP or ddGTP:ddTTP, either pair of which will result in complete sequence information about the entire template sequence lying between the 3' ends of the primers.

Each of the ddNTPs is initially present in a concentration of between about 0.01 $\mu$M to 10 mM. In a preferred embodiment, the concentration of each ddNTP is between about 100 $\mu$M and 500 $\mu$M. The concentration of the pairs of ddNTPs used in the fragment producing reaction depends upon the efficiencies of the ddNTP to be used as a substrate for the polymerase, as will be understood by those with skill in the art with reference to this disclosure.

The reaction mixture also comprises a buffer having sufficient buffering capacity to maintain the pH of the reaction mixture over a pH range of about 6.0 to 10.0 and over a temperature range of about 20° C. to 98° C. In a preferred embodiment, the buffer is Tris at a concentration of between about 10 mM and 500 mM, and preferably between about 50 mM and 300 mM.

The reaction mixture further comprises at least one divalent cation. In a preferred embodiment, the divalent cation is magnesium chloride salt in a final concentration of between about 0.5 and 10 mM, and more preferably in a final concentration of between about 1.5 and 3.0 mM. Manganese chloride salt in a concentration of between about 0.1 mM and 20 mM can also be used as appropriate.

The reaction mixture additionally comprises a polymerase, such as a DNA dependant DNA polymerase. The polymerase selected should preferably be thermostable, have minimal exonuclease, endonuclease or other DNA degradative activity, and should have good efficiency and fidelity for the incorporation of ddNTPs into the synthesizing DNA strands. A suitable concentration of polymerase is between about 0.1 and 100 units per reaction, and more preferably a concentration of between about 1 and 10 units per reaction. Suitable polymerases are commercially available from Amersham Pharmacia Biotech, Inc., Promega Corporation, Madison, Wis., US and Perkin-Elmer Corporation, among other suppliers.

In a preferred embodiment, the reaction mixture comprises additional substances to improve yield or efficiency, enhance polymerase stability, and to alleviate artifacts. For example, other dNTPs or supplemental dNTPs such as deoxyinosine triphosphate (dITP) or 7-deaza GTP can be employed in a concentration of between about 0.1 mM and 20 mM in place of dGTP to alleviate compression, stutters or stops that can occur in the fragment producing reaction. Also, for example, detergents and reducing agents can be added to stabilize the polymerase. Additionally, organic solvents such as glycerol, dimethylformamide, formamide, acetontrile and isopropanol can be added to the reaction mixture to improve annealing stringency of the primers. When present, the organ solvents preferably have a concentration of between about 0.1% and 20% by volume.

In addition to the above discussed reaction mixture components, it is essential that the reaction products produced by the fragment producing reaction contain at least one detectible label by incorporation of labeled primers, labeled dideoxyterminators or labeled nonterminating deoxynucleotides, or a combination of the foregoing, depending on the number and types of samples being analyzed, and whether the samples are from pooled sources, as will be understood with reference to this disclosure. Among the types of labels suitable for performing the present method are fluorescent labels, fluorescent energy transfer labels, luminescent labels, chemiluminescent labels, phosphorescent labels and photoluminescent labels, though other types of labels are suitable as long as the labels are compatible with this method, the detection of multiple labels permits the discrimination of the labels from one another, and the reaction products can be measured by the labels. In a preferred embodiment, the label is either a fluorescent label or a fluorescent energy transfer label.

A wide variety of fluorescent labels, such as fluorescent dyes, are suitable for use in this method. Suitable fluorescent labels suitable should be chemically stable for their incorporation into the labeled reagents, and should be resistant to degradation during performance of this method. Further, the fluorescent labels should have only nominal influence on the migration of the reaction products when the reaction products are being analyzed. Additionally, the fluorescent labels should have good quantum efficiency for excitation and emission, and the spectral separation between the excitation wavelength and the emission wavelength should be at least 10 nanometers where they are capable of being spectrally resolved from one another at their emission wavelength having a minimum of 5 nanometers between their respective emissions. The excitation wavelengths are preferably between about 260 nm and 2000 nm and the emission wavelengths are preferably between about 280 nm and 2500 nm. Further, the fluorescent labels should preferably be capable of being attached to the primers, dNTPs and ddNTPs.

Examples of suitable fluorescent labels are fluorescent compounds derived from the family of fluoresceine and its derivatives, rhodamine and its derivatives, Bodipy® (4,4-difluoro-4-bora-3a,4a-diaza-s-indacene) and its derivatives, cyanine and its derivatives, and Europium chelates. Suitable fluorescent dye labels are commercially available from Molecular Probes, Inc., Eugene, Oreg., US and Research Organics, Inc., Cleveland, Ohio., US, among other sources. Similarly, suitable energy transfer pairs are commercially available, such as Big Dyes™ from Perkin-Elmer Corporation. Further, custom-made primers with attached energy transfer pairs can be obtained from Amersham Pharmacia Biotech, Inc., among other suppliers.

The primers used in the reaction mixture can be labeled at their 5' ends or internally with one or more labels as long as the 3'OH groups of the primers remain exposed to allow the polymerase to function with the primer. While both forward and reverse primers can be labeled with identical labels, it is preferred that the forward and reverse primers are labeled with different labels that can be distinguished from each another.

Suitable labeled primers can be prepared by any of several methods, or can be purchased commercially, as will be understood by those with skill in the art with reference to this disclosure. For example, fluorescent phosphoramidites can be used either to label the 5' end of the primers or to internally label the primers. The primary amines can be labeled using standard N-hydroxy succinimide esters or other species of the fluorescent dyes reactive with the primary amines can be introduced into the primers as the primers are synthesized. Further, other reactive species such as sulfhydryl groups can be introduced into the primers and conjugated to fluorescent dyes having appropriate reactivities. A typical concentration of dye labeled primers for use in this method would be between about 1 pMole and 50 pMoles for a 20 µl reaction volume.

The dideoxyterminator triphosphates used in the reaction mixture are labeled. The labeled ddNTPs terminate polynucleotide strand synthesis in the fragment producing reaction, as well as allow identification of the base at which strand termination occurs in the reaction products.

Each member of a ddNTP pair should be labeled differently, such as having a different fluorophore, so that each member of a ddNTP pair can be detected, distinguished and measured separately. Further, each member of a labeled ddNTP pair, such as ddATP and ddCTP, can have differently labeled subsets for each fragment producing reaction performed, such as x1ddA, x2ddA . . . xnddA and y1ddC, y2ddC . . . ynddC, respectively, where x1, x2, . . . xn and y1, y2, . . . yn each represents different labels conjugated to the respective ddNTP, to allow further identification of the reaction products. Suitable labels include fluorescein, rhodamine 110, rhodamine 6G and carboxyrhodamine, among other labels. Suitable labeled ddNTPs are commercially available from Amersham Pharmacia Biotech, Inc. and Perkin-Elmer Corporation, among other suppliers.

In a preferred embodiment, the concentration of fluorescently labeled ddNTPs for use in this method would be between about 10 $\mu$M to 1 mM, and more preferably between about 10 $\mu$M and 300 $\mu$M. However, the concentration of each type of labeled ddNTP of a pair of ddNTPs need not be equal to one another. Rather, the concentrations will preferably be optimized according to techniques known to those with skill in the art for reaction product length, signal strength and the respective efficiencies of the ddNTP as a substrate for the polymerases utilized.

Further, the deoxynucleotide triphosphates used in the reaction mixture can similarly be labeled to identify the reaction mixture which produced reaction products. This is accomplished by labeling all labeled dNTPs used in a single fragment producing reaction with the same label, while labeling all labeled dNTPs used in a different fragment producing reaction with a different distinguishable label. When used, labeled dNTPs constitute only a fraction of the total amount of dNTPs. When used, labeled dNTPs are preferably present at a ratio of about 1% to 10% of the concentration of unlabeled dNTPs. In a preferred embodiment, the dNTPs are fluorescently labeled.

Once the reaction mixture is placed in the appropriate vessel, the fragment producing reaction is accomplished according to techniques known to those with skill in the art, such as by standard PCR techniques using temperature cycling. This fragment producing reaction produces a set of labeled reaction products comprising a family of labeled complementary DNA strands terminated at every location beyond the primer by a dideoxyterminator at the 3' end where one of the nucleotides in the template strands contains a base corresponding to one of the terminators pairs.

By way of example only, typical times and temperatures required to accomplish the cycling conditions are a temperature over the range of 90° C. to 98° C. for a period of 10 seconds to 2 minutes for melting the template strands; a temperature range of 40° C. to 60° C. for an interval ranging from 1 second to 60 seconds to anneal the primers to their respective target strands; and a temperature range of 50° C. to 75° C. for an interval ranging from 30 seconds to 10 minutes to extend the primers by the action of the DNA polymerase. These cycles are repeated a sufficient number of times, generally between about 10 and 60 times, to obtain sufficient quantities of detectable labeled reaction products. In a preferred embodiment, the fragment producing reaction is performed using 25 cycles at 95° C. for 30 seconds, 50° C. for 5 seconds and 60° C. for 4 minutes. However, as will be understood by those with skill in the art with reference to this disclosure, the optimum times and temperatures will depend on the primer lengths, primer sequence, polynucleotide sequence being analyzed and the DNA polymerase utilized.

6) Analysis of Reaction Products:

After production of the family of labeled, linear polynucleotide fragments from both strands of the template, these labeled reaction products from the first polynucleotide are identified using the labels and the identity is compared to a known reference sequence or compared with the labeled reaction products produced from a second polynucleotide to determine the sequence variation between the first polynucleotide and the reference sequence or between the first polynucleotide and the second polynucleotide. This is accomplished as follows.

First, preferably, the labeled reaction products are purified from the other reaction mixture components by methods well known to those in the art, such as by ethanol precipitation. The purified labeled reaction products are then analyzed by an appropriate process using an appropriate instrument. The processes and instruments used for such an analysis must be capable of detecting and discriminating between the labels utilized in the fragment producing reaction method and must be capable of discriminating or resolving a single base difference between strands of single stranded DNA of different lengths.

For example, the purified labeled reaction products can be combined with suitable loading reagents and then analyzed using denaturing electrophoresis under conditions similar to the those for standard polynucleotide sequencing. In summary, the reaction products are dissolved in water or other suitable buffer and are mixed with formamide.

Then, they are denatured by heating at 95° C. for about 1 to 5 minutes and rapidly cooled at 4° C. Next, the denatured reaction products are loaded onto an appropriate instrument and analyzed using denaturing polyacrylamide electrophoresis or denaturing capillary electrophoresis or other suitable method where the instrument used is capable of detecting and distinguishing the labels on the reaction products. The separation matrix used for the electrophoresis must be capable of single base resolution for single stranded or denatured DNA. Suitable instrumentation is commercially available from Amersham Pharmacia Biotech, Inc., LiCor, Inc., Lincoln, Neb., US and Perkin-Elmer Corporation, among other sources. Additionally, suitable custom-made instruments are also available, such as the SCAFUD from the Marshfield Institute, Marshfield, Wis., US. Both types of instruments have software for the analysis of the patterns produced by the detection of the fluorescent reaction products and for comparing the resulting data for each sample undergoing detection and analysis.

Once the labeled reaction products are analyzed, they are compared to a reference sequence or to similar reaction products from a second polynucleotide analyzed and the variations between the first polynucleotide and a reference sequence or between the first polynucleotide and the second analyzed polynucleotide can be determined. Additionally, the results of multiple analyses, and the sources and phenotypes of the samples can be compiled into data bases for additional analysis and correlation. Further, more than two polynucleotides sequence can be simultaneously analyzed using this method in the a single reaction mixture, as will be understood by those with skill in the art with reference to this disclosure.

7) Interpretation of Labels Incorporated into Reaction Products:

The preferred modes of detection of the labeled reaction products produced by the present method detect and discriminate between the labels used in the method. The labels serve two different functions.

First, source-identifying labels are used to identify the source of the sequences represented by the reaction products by incorporating different, distinguishably labeled primers or labeled nonterminating dNTPs, or both, into the reaction products, where the same label is incorporated into reaction products derived from a single source or pool. Identifying the signal from these labels then allows determination of the source or pool from which the reaction product sequences were derived.

Secondly, base-identifying labels, which are different labels from the source-identifying labels, are used to identify the terminal base on a reaction product by incorporating different, distinguishably labeled dideoxyterminators into the reaction products.

The uses of these two types of labels will be better understood by reference to the following examples. In the first example, the forward primer used in the fragment producing reaction has a red label (R) and the reverse primer used in the fragment producing reaction has a blue label (B). Further, the ddGTP member of the pair of dideoxyterminators has a green label (G), and the ddTTP member of the pair of dideoxyterminators has a yellow label (Y). In addition, a portion of the nonterminating dCTPs have orange labels (O) for the fragment producing reaction containing templates from a first sample, and purple labels (P) for the fragment producing reaction containing templates from a second sample. Table I gives the expected results of the two fragment producing reactions and shows the distribution of labeled reaction products expected in this example.

TABLE I

| First Sample | | | | Second Sample | | | |
|---|---|---|---|---|---|---|---|
| dCTP Sample Color | Primer and Color | Terminator and Color | Reaction Product Colors | dCTP Sample Color | Primer and Color | Terminator and Color | Reaction Product Colors |
| O | Forward-R | ddGTP-G | O, R, G | P | Forward-R | ddGTP-G | P, R, G |
| O | Forward-R | ddTTP-Y | O, R, Y | P | Forward-R | ddTTP-Y | P, R, Y |
| O | Reverse-B | ddGTP-G | O, B, G | P | Reverse-B | ddGTP-G | P, B, G |
| O | Reverse-B | ddTTP-Y | O, B, Y | P | Reverse-B | ddTTP-Y | P, B, Y |

Thus, as can be appreciated from the above example, each reaction product can be identified as to its sample source, template strand and terminating base, while the location of the terminal base can be identified from the analysis of the length of the reaction products in combination with knowledge of the length of the template strand. In the above example, peaks with the colors orange, red and green within them arise from reaction products from the first sample because they contain orange, are from the forward primer containing template strands because they contain red, and are each terminated by base G because they contain green.

By considering the labels of the reaction products generating each peak and their relative positions from one another, a sequence for both the forward and reverse strands of the template can be determined. The sample from which the reaction products derived can be identified by their label and the sequence variations between a polynucleotide from a first sample and a polynucleotide from a second sample can be determined. Further, by analyzing relative intensities of peaks generated from the labeled reaction products from the two samples, an estimate of the relative frequency of the occurrence of the variation can be determined.

In the second example, the location of a polynucleotide variation on a single allele or on two alleles is determined. For this purpose, the fragment producing reaction is performed with entirely unlabeled dNTPs, but the forward primer used in the fragment producing reaction has a red label (R) and the reverse primer used in the fragment producing reaction has a blue label (B). Further, the ddGTP member of the pair of dideoxyterminators has a green label (G), and the ddTTP member of the pair of dideoxyterminators has a yellow label (Y). Table II gives the expected results and shows the distribution of labeled reaction products expected in this example.

TABLE II

| First Allele | | | Second Allele | | |
|---|---|---|---|---|---|
| Primer and Color | Terminator and Color | Reaction Products Colors | Primer and Color | Terminator and Color | Reaction Product Colors |
| Forward-R | ddGTP-G | R, G | Forward-R | ddGTP-G | R, G |
| Forward-R | ddTTP-Y | R, Y | Forward-R | ddTTP-Y | R, Y |
| Reverse-B | ddGTP-G | B, G | Reverse-B | ddGTP-G | B, G |
| Reverse-B | ddTTP-Y | B, Y | Reverse-B | ddTTP-Y | B, Y |

By reference to the known sequence, the peaks from the various reaction products can be determined to derive from either the forward or reverse strands. Then, a comparison of the resulting products arising from forward and reverse strands and their relative intensities and color allow a determination to be made as to whether the variation is present on one allele or two alleles.

EXAMPLE I

USING THE PRESENT METHOD TO LOCATE AND IDENTIFY AN SNP FROM A SINGLE DNA SAMPLE FROM AN INDIVIDUAL

The present method was used to determine the location and identity of two different single nucleotide polymorphisms in a region of DNA containing both the human growth hormone transcriptional activator (GHDTA) and the human growth hormone (GH1) genes. The method was performed separately on DNA from two different individuals. One individual was homozygous A at both loci 1 and 2. The other individual was homozygous G at loci 1 and homozygous T at loci 2. The method was performed as follows.

First, 2.7 kb templates spanning the region containing the GHDTA and GH1 genes from each individual were separately prepared using PCR by standard methods. Then, fragment producing reactions were performed. The reaction mixtures contained fluorescent labeled 2'-3'dideoxynucleotide triphosphates terminator pairs. Two reactions were performed on each sample. One reaction was performed using the pair ddATP:ddCTP (the "A/C reaction") and another reaction was performed using the pair ddGTP:ddTTP (the "G/T reaction").

Each reaction mixture contained components from an Amersham ThermoSequenase™ Dye Terminator Cycle Sequencing Core Kit according to the manufacturer's instructions, which comprised 1/10 the amount of the following components: 20 $\mu$l of 5×reaction buffer, 10 $\mu$l of dNTP mix, 20 $\mu$l deionized water, 10 $\mu$l of ThermoSequenase , 120–150 ng of template, and 20 pMoles each of forward and reverse primers which spanned a 272 base pair sequence of the template between the primers' 5' ends. The A/C reactions also contained 1 $\mu$l of rhodamine 6G labeled ddATP and 1 $\mu$l of ROX labeled ddCTP. The G/T reactions also contained 1 $\mu$l of rhodamine 110 labeled ddGTP and 1 $\mu$l of TAMRA labeled ddTTP.

A wax bead overlay was used to prevent evaporation during thermocycling. Cycles used in the fragment producing reaction consisted of an initial denaturation of 3.5 minutes at 96° C., an annealing of 15 seconds at 50° C., and an extension of 4 minutes at 60° C. Then, thirty additional cycles were performed consisting of 30 seconds at 96° C., 15 seconds at 50° C. and 4 minutes at 60° C. with a final extension of 10 minutes at 60° C.

Following cycling, the reaction mixture was chilled to 4° C. The wax overlay was removed and the reaction products were transferred to 1.5 ml tubes. Then, the DNA was precipitated by addition of 2 $\mu$l of 3M sodium acetate (pH 5.2) and 68 $\mu$l of −20° C., 100% ethanol. The tubes were chilled to −20° C. for 10 minutes and then centrifuged for 5 minutes at 13,500×g.

Next, the ethanol was aspirated from the pellets and the pellets were washed with 300 $\mu$l of −20° C., 80% ethanol and centrifuged for 5 minutes at 13,500×g. The ethanol was aspirated and the pellets were briefly dried, then resuspended in 4 $\mu$l of deionized water. For the A/C and G/T sets, 2 $\mu$l of an internal standard MapMarker™ 400 (BioVentures, Inc., Murfreesboro, Tenn.) labeled with TAMRA or ROX was added, respectively. The samples were vortexed and then heated for 10 minutes at 37° C. to completely dissolve the pellets. The samples were briefly centrifuged to bring reaction products to the bottom of the tubes.

2 $\mu$l of each sample containing the reaction products was added to 10 $\mu$l of deionized formamide in 0.5 ml analysis tubes and capped with septa. The tubes were vortexed and briefly centrifuged. Then, the samples were denatured for 5 minutes at 95° C. and quickly chilled to 4° C.

Next, the reaction products were analyzed on an ABI PRISM™ 310 Genetic Analyzer from Perkin-Elmer Corporation using a 41 cm uncoated column and POP 4 gel. The run module for the analyses comprised electrokinetic injection at 5 kV for 30 seconds, and electrophoresis at 15 kV for 24 minutes at 60° C. using appropriate spectral CCD modules for the dye sets. These conditions were utilized to resolve the fluorescently labeled reaction products. Data was processed using GeneScan7 analysis software from Perkin-Elmer Corporation, according to the manufacturer's instructions. For the A/C reactions, the channels corresponding to green (ddA Rhodamine 6G) and red (ddC ROX) were utilized for sample data, and the yellow (TAMRA) channel was utilized for the internal standard. For the G/T reactions, the blue, (ddG Rhodamine 110) and the yellow ddTTP (TAMRA) channels were utilized for sample data, and the red (ROX) channel was utilized for the internal standard.

The results obtained for each reaction were compared to the known DNA sequence for each of the individuals in the region flanked by the primers, and comparison demonstrated the proper location and identity of the SNPs. This demonstrates that the present method can be used to locate and identify a plurality of SNPs from a DNA sample from an individual.

EXAMPLE II

USING THE PRESENT METHOD TO LOCATE AND IDENTIFY AN SNP FROM POOLED TEMPLE MIXTURES AND FROM POOLED GENOMIC DNA SAMPLES

The present method was further used to locate and identify SNPs in mixtures of pooled templates, and in mixtures of pooled genomic DNA. First, mixtures of pooled 2.7 kb templates, each obtained as disclosed in Example I, were made using 150 ng/µl total DNA in the following template ratios: 1:0; 40:1; 20:1; 10:1; 1:1; 1:10; 1:20; 1:40; 0:1. Each of these pooled template mixtures was subjected to the present method as further disclosed in Example I. One reaction was performed using a ddATP:ddCTP terminator pair, and another reaction was performed using a ddGTP:ddTTP terminator pair. The reaction products were analyzed as in Example I.

The results demonstrated that the location and identity of the SNPs were determined by the present method even though the reaction mixtures contained pooled templates, and even when the templates were diluted as much as 1 in 40 with templates having the other alleles. Further, the relative intensities of peaks corresponding to each allele accurately represented the proportion of each allele in the reaction mixtures. This indicates that the frequency of an SNP in a pooled template mixture can be determined using the present method.

Second, mixtures of genomic DNAs from the same two individuals in Example I with different SNP genotypes were pooled in ratios of 1:0; 40:1; 20:1; 10:1; 1:1; 1:10; 1:20; 1:40; 0:1. This pooled genomic DNA was then used to obtain 2.7 kb templates. 120 ng total aliquots of the templates were purified and processed according to the present method as disclosed in Example I but using primers and using ddGTP:ddTTP terminator pairs, all of which were fluorescently tagged with different, distinctly identifiable fluorochromes.

The results produced distinctly identifiable patterns for each of the two templates. Two color tagged fragments appeared and their signal intensities vary with the proportion of the SNP found in the pooled mixture. That is, as the proportion of SNP1 (G) and SNP2 (T) alleles or the proportion of SNP1(A) and SNP2(A) increased or decreased, the signals associated the terminators on the corresponding fragments also similarly increased or decreased.

In contrast to uncolored ddF patterns produced by radiolabelling, this example demonstrates that patterns resulting from the present method can easily locate and identify different SNPs because the terminators were tagged with different fluorochromes which could be selectively identified by their color differences. Further, the reaction products resulting from SNPs were easily identified even when the templates were pooled or when pools of genomic DNA were used to produce pooled templates containing the SNP, and when the templates containing the SNP were diluted to as much as 1:40 with templates that did not contain the SNP.

Although the present invention has been discussed in considerable detail with reference to certain preferred embodiments, other embodiments are possible. Therefore, the spirit and scope of the appended claims should not be limited to the description of preferred embodiments contained herein.

What is claimed is:

1. A method of determining the presence and identity of a variation in a nucleotide sequence between a first polynucleotide and a second polynucleotide, comprising:
   a) providing a sample of the first polynucleotide;
   b) selecting a region of the first polynucleotide potentially containing the variation;
   c) subjecting the selected region to a template producing amplification reaction to produce a first plurality of double stranded polynucleotide templates which include the selected region;
   d) selecting a region of the templates potentially containing the variation;
   e) producing a first family of labeled, linear polynucleotide fragments from both strands of the templates simultaneously by a fragment producing reaction including,
      i) a set of at least two primers comprising a first primer and a second primer,
      ii) at least four types of nucleotide triphosphates, comprising at least two different sets of two Watson-Crick-pairing bases, and
      iii) two types of fragment terminators, comprising a first terminator and a second terminator;
      where the first primer and the second primer flank the selected region of the template strands;
      where the first primer has a first primer label and the second primer has a second primer label;
      where at least a portion of one of the types of nucleotide triphosphates is labeled with a first nucleotide label;
      where the first terminator and the second terminator are non-Watson-Crick-pairing;
      where the first terminator is labeled with a first terminator label and the second terminator is labeled with a second terminator label;
      where each of the first primer label, the second primer label, the first nucleotide label, the first terminator label and the second terminator label are all distinguishable from each other;
      where each of the first family of fragments are terminated by either the first terminator or the second terminator at the 3' end of the fragment; and
      where the first family of fragments include at least one fragment terminating at each possible base, represented by the either the first terminator or the second terminator, of that portion of the selected region of both template strands flanked by a primer; and
   f) determining the location and identity of the bases in the selected region of the first polynucleotide by detecting the first primer label, the second primer label, the first nucleotide label, the first terminator label and the second terminator label present in the fragments.

2. The method of claim 1, additionally comprising comparing the location and identity of the bases determined with the location and identity of bases from a second polynucleotide, thereby identifying the presence and identity of a variation in a nucleotide sequence between the selected region of the first polynucleotide and a corresponding region of the second polynucleotide, after determining the location and identity of the bases in the selected region of the first polynucleotide.

3. The method of claim 1, where the selected region of the first polynucleotide comprises a plurality of discontinuous sequences on the first polynucleotide.

4. The method of claim 1, where the template producing amplification reaction comprises subjecting the selected region to PCR.

5. The method of claim 1, where the template producing amplification reaction comprises subjecting the selected region to RT-PCR.

6. The method of claim 1, where the first plurality of double stranded polynucleotide templates comprise double stranded nucleic acid strands of between about 50 and 50,000 nucleotides per strand.

7. The method of claim 1, further comprising purifying the temples to remove other amplification reaction components after subjecting the selected region to a template producing amplification reaction.

8. The method of claim 1, where the fragment producing amplification reaction comprises subjecting the selected region to PCR.

9. The method of claim 1, where the fragment producing amplification reaction comprises subjecting the selected region to RT-PCR.

10. The method of claim 1, where the selected region of the template strands is between about 100 and 1000 nucleotides per strand.

11. The method of claim 1, where the at least four types of nucleotide triphosphates comprises dATP, dCTP, dGTP and dTTP.

12. The method of claim 1, where the at least four types of nucleotide triphosphates comprises dATP, dCTP, dGTP and dUTP.

13. The method of claim 1, where the terminators are 2'-3'-dideoxyterminators.

14. The method of claim 1, where the first terminator comprises a pyrimidine nucleotide and where the second terminator comprises a purine nucleotide.

15. The method of claim 1, where the first terminator and the second terminator are selected from the group consisting of ddATP:ddCTP, ddATP:ddGTP, ddCTP:ddTTP and ddGTP:ddTTP.

16. The method of claim 1, where the first terminator and the second terminator are selected from the group consisting of ddATP:ddCTP, ddATP:ddGTP, ddCTP:ddUTP and ddGTP:ddUTP.

17. The method of claim 1, where first primer label, the second primer label, the first nucleotide label, the first terminator label and the second terminator label are selected from the group consisting of fluorescent labels, fluorescent energy transfer labels, luminescent labels, chemiluminescent labels, phosphorescent labels and photoluminescent labels.

18. The method of claim 1, where the portion of one of the types of nucleotide triphosphates that is labeled with a first nucleotide label comprises between about 1% and about 10% of the total concentration of unlabeled nucleotide triphosphates.

19. The method of claim 1, further comprising purifying the labeled reaction products from the fragment producing reaction before determining the location and identity of the bases in the selected region of the first polynucleotide.

20. The method of claim 1, where the sequence of the corresponding region of the second polynucleotide is determined by:

a) providing a sample of the second polynucleotide;
b) selecting a region of the second polynucleotide which corresponds to the region of the first polynucleotide potentially containing the variation;
c) subjecting the corresponding region of the second polynucleotide to a template producing amplification reaction to produce a second plurality of double stranded polynucleotide templates which include the corresponding region;
d) producing a second family of labeled, linear polynucleotide fragments from both strands of the template simultaneously by a fragment producing reaction including,
   i) a set of at least two primers comprising a third primer and a fourth primer,
   ii) at least four types of nucleotide triphosphates, comprising at least two different sets of two Watson-Crick-pairing bases,
   iii) two types of fragment terminators, comprising a third terminator and a fourth terminator;
   where the third primer and the fourth primer flank the selected region of the template strands;
   where the first terminator and the second terminator are non-Watson-Crick-pairing;
   where each of the family of fragments are terminated by either the first terminator or the second terminator at the 3' end of the fragment; and
   where the family of fragments include at least one fragment terminating at each possible base, represented by the either the first terminator or the second terminator, of that portion of the selected region of both template strands flanked by a primer;
e) determining the location and identity of at least some of the bases in the corresponding region of the second polynucleotide.

21. The method of claim 20, where the sequence of the corresponding region of the second polynucleotide is determined simultaneously with determining the location and identity of the bases in the selected region of the first polynucleotide.

22. The method of claim 20, where producing the first family of labeled, linear polynucleotide fragments and producing the second family of labeled, linear polynucleotide fragments is performed in one reaction.

23. The method of claim 20, where the third primer has a third primer label and the fourth primer has a fourth primer label, and where the third primer label and the fourth primer label are all distinguishable from each other.

24. The method of claim 20, where at least a portion of one of the types of nucleotide triphosphates in the production of the second family of labeled, linear polynucleotide fragments is labeled with a second nucleotide label.

25. The method of claim 20, where the third terminator is labeled with a third terminator label and the fourth terminator is labeled with a fourth terminator label, and where the third terminator label and the fourth terminator label are all distinguishable from each other.

26. The method of claim 20, where the third primer has a third primer label, the fourth primer has a fourth primer label and at least a portion of one of the types of nucleotide triphosphates in the production of the second family of labeled, linear polynucleotide fragments is labeled with a second nucleotide label, and where the third primer label, the fourth primer label and the second nucleotide label are all distinguishable from each other.

27. The method of claim 20, where the third primer has a third primer label, the fourth primer has a fourth primer label, the third terminator is labeled with a third terminator label and the fourth terminator is labeled with a fourth terminator label, and where the third primer label, the fourth primer label, the third terminator label and the fourth terminator label are all distinguishable from each other.

28. The method of claim 20, where at least a portion of one of the types of nucleotide triphosphates in the production of the second family of labeled, linear polynucleotide fragments is labeled with a second nucleotide label, where the third terminator is labeled with a third terminator label and the fourth terminator is labeled with a fourth terminator label, and where the second nucleotide label, the third terminator label and the fourth terminator label are all distinguishable from each other.

29. The method of claim 20, where the third primer has a third primer label, the fourth primer has a fourth primer label, at least a portion of one of the types of nucleotide triphosphates in the production of the second family of labeled, linear polynucleotide fragments is labeled with a second nucleotide label, the third terminator is labeled with a third terminator label and the fourth terminator is labeled with a fourth terminator label, and where the third primer label, the fourth primer label, the second nucleotide label, the third terminator label and the fourth terminator label are all distinguishable from each other.

30. A method of determining the presence and identity of a variation in a nucleotide sequence between a first polynucleotide and a second polynucleotide, comprising:
   a) providing a sample of the first polynucleotide;
   b) selecting a region of the first polynucleotide potentially containing the variation;
   c) subjecting the selected region to a template producing amplification reaction to produce a first plurality of double stranded polynucleotide templates which include the selected region;
   d) selecting a region of the templates potentially containing the variation;
   e) producing a first family of labeled, linear polynucleotide fragments from both strands of the templates simultaneously by a fragment producing reaction including,
      i) a set of at least two primers comprising a first primer and a second primer,
      ii) at least four types of nucleotide triphosphates, comprising at least two different sets of two Watson-Crick-pairing bases, and
      iii) two types of fragment terminators, comprising a first terminator and a second terminator;
         where the first primer and the second primer flank the selected region of the template strands;
         where the first terminator and the second terminator are non-Watson-Crick-pairing;
         where each of the first family of fragments are terminated by either a first terminator or a second terminator at the 3' end of the fragment; and
         where the first family of fragments include at least one fragment terminating at each possible base, represented by the either the first terminator or the second terminator, of that portion of the selected region of both template strands flanked by a primer; and
   f) determining the location and identity of the bases in the selected region.

31. The method of claim 30, additionally comprising comparing the location and identity of the bases determined with the location and identity of bases from a second polynucleotide, thereby identifying the presence and identity of a variation in a nucleotide sequence between the selected region of the first polynucleotide and a corresponding region of the second polynucleotide, after determining the location and identity of the bases in the selected region of the first polynucleotide.

32. The method of claim 30, where the first primer has a first primer label and the second primer has a second primer label, and where the first primer label and the second primer label are all distinguishable from each other.

33. The method of claim 30, where at least a portion of one of the types of nucleotide triphosphates is labeled with a first nucleotide label.

34. The method of claim 30, where the first terminator is labeled with a first terminator label and the second terminator is labeled with a second terminator label, and where the first terminator label and the second terminator label are all distinguishable from each other.

35. The method of claim 30, where the first primer has a first primer label, the second primer has a second primer label and at least a portion of one of the types of nucleotide triphosphates is labeled with a first nucleotide label, and where the first primer label, the second primer label and the first nucleotide label are all distinguishable from each other.

36. The method of claim 30, where the first primer has a first primer label, the second primer has a second primer label, the first terminator is labeled with a first terminator label and the second terminator is labeled with a second terminator label, and where the first primer label, the second primer label, the first terminator label and the second terminator label are all distinguishable from each other.

37. The method of claim 30, where at least a portion of one of the types of nucleotide triphosphates is labeled with a first nucleotide label, where the first terminator is labeled with a first terminator label and the second terminator is labeled with a second terminator label, and where the first nucleotide label, the first terminator label and the second terminator label are all distinguishable from each other.

38. The method of claim 30, where the first primer has a first primer label, the second primer has a second primer label, at least a portion of one of the types of nucleotide triphosphates is labeled with a first nucleotide label, the first terminator is labeled with a first terminator label and the second terminator is labeled with a second terminator label, and where the first primer label, the second primer label, the first nucleotide label, the first terminator label and the second terminator label are all distinguishable from each other.

39. The method of claim 30, where the selected region of the first polynucleotide comprises a plurality of discontinuous sequences on the first polynucleotide.

40. The method of claim 30, where the template producing amplification reaction comprises subjecting the selected region to PCR.

41. The method of claim 30, where the template producing amplification reaction comprises subjecting the selected region to RT-PCR.

42. The method of claim 30, where the first plurality of double stranded polynucleotide templates comprise double stranded nucleic acid strands of between about 50 and 50,000 nucleotides per strand.

43. The method of claim 30, further comprising purifying the temples to remove other amplification reaction components after subjecting the selected region to a template producing amplification reaction.

44. The method of claim 30, where the fragment producing amplification reaction comprises subjecting the selected region to PCR.

45. The method of claim 30, where the fragment producing amplification reaction comprises subjecting the selected region to RT-PCR.

46. The method of claim 30, where the selected region of the template strands is between about 100 and 1000 nucleotides per strand.

47. The method of claim 30, where the at least four types of nucleotide triphosphates comprises dATP, dCTP, dGTP and dTTP.

48. The method of claim 30, where the at least four types of nucleotide triphosphates comprises dATP, dCTP, dGTP and dUTP.

49. The method of claim 30, where the terminators are 2'-3'-dideoxyterminators.

50. The method of claim 30, where the first terminator comprises a pyrimidine nucleotide and where the second terminator comprises a purine nucleotide.

51. The method of claim 30, where the first terminator and the second terminator are selected from the group consisting of ddATP:ddCTP, ddATP:ddGTP, ddCTP:ddTTP and ddGTP:ddTTP.

52. The method of claim 30, where the first terminator and the second terminator are selected from the group consisting of ddATP:ddCTP, ddATP:ddGTP, ddCTP:ddUTP and ddGTP:ddUTP.

53. The method of claim 30, where first primer label, the second primer label, the first nucleotide label, the first terminator label and the second terminator label are selected from the group consisting of fluorescent labels, fluorescent energy transfer labels, luminescent labels, chemiluminescent labels, phosphorescent labels and photoluminescent labels.

54. The method of claim 30, where the portion of one of the types of nucleotide triphosphates that is labeled with a first nucleotide label comprises between about 1% and about 10% of the total concentration of unlabeled nucleotide triphosphates.

55. The method of claim 30, further comprising purifying the labeled reaction products from the fragment producing reaction before determining the location and identity of the bases in the selected region of the first polynucleotide.

56. The method of claim 30, where one or more of the first primer, the second primer, a portion of one of the types of nucleotide triphosphates, the first terminator and the second terminator is labeled, and where determining the location and identity of the bases in the selected region of the first polynucleotide is accomplished by detecting the label or labels.

57. The method of claim 30, where the sequence of the corresponding region of the second polynucleotide is determined by:
a) providing a sample of the second polynucleotide;
b) selecting a region of the second polynucleotide which corresponds to the region of the first polynucleotide potentially containing the variation;
c) subjecting the corresponding region of the second polynucleotide to a template producing amplification reaction to produce a second plurality of double stranded polynucleotide templates which include the corresponding region;
d) producing a second family of labeled, linear polynucleotide fragments from both strands of the template simultaneously by a fragment producing reaction including,
i) a set of at least two primers comprising a third primer and a fourth primer,
ii) at least four types of nucleotide triphosphates, comprising at least two different sets of two Watson-Crick-pairing bases; and
iii) two types of fragment terminators, comprising a third terminator and a fourth terminator;
where the third primer and the fourth primer flank the selected region of the template strands;
where the first terminator and the second terminator are non-Watson-Crick-pairing;
where each of the family of fragments are terminated by either a first terminator or a second terminator at the 3' end of the fragment; and
where the family of fragments include at least one fragment terminating at each possible base, represented by the either the first terminator or the second terminator, of that portion of the selected region of both template strands flanked by a primer;
e) determining the location and identity of at least some of the bases in the corresponding region of the second polynucleotide.

58. The method of claim 57, where the sequence of the corresponding region of the second polynucleotide is determined simultaneously with determining the location and identity of the bases in the selected region of the first polynucleotide.

59. The method of claim 57, where producing the first family of labeled, linear polynucleotide fragments and producing the second family of labeled, linear polynucleotide fragments is performed in one reaction.

60. The method of claim 57, where the third primer has a third primer label and the fourth primer has a fourth primer label, and where the third primer label and the fourth primer label are all distinguishable from each other.

61. The method of claim 57, where at least a portion of one of the types of nucleotide triphosphates in the production of the second family of labeled, linear polynucleotide fragments is labeled with a second nucleotide label.

62. The method of claim 57, where the third terminator is labeled with a third terminator label and the fourth terminator is labeled with a fourth terminator label, and where the third terminator label and the fourth terminator label are all distinguishable from each other.

63. The method of claim 57, where the third primer has a third primer label, the fourth primer has a fourth primer label and at least a portion of one of the types of nucleotide triphosphates in the production of the second family of labeled, linear polynucleotide fragments is labeled with a second nucleotide label, and where the third primer label, the fourth primer label and the second nucleotide label are all distinguishable from each other.

64. The method of claim 57, where the third primer has a third primer label, the fourth primer has a fourth primer label, the third terminator is labeled with a third terminator label and the fourth terminator is labeled with a fourth terminator label, and where the third primer label, the fourth primer label, the third terminator label and the fourth terminator label are all distinguishable from each other.

65. The method of claim 57, where at least a portion of one of the types of nucleotide triphosphates in the production of the second family of labeled, linear polynucleotide fragments is labeled with a second nucleotide label, where the third terminator is labeled with a third terminator label and the fourth terminator is labeled with a fourth terminator label, and where the second nucleotide label, the third terminator label and the fourth terminator label are all distinguishable from each other.

66. The method of claim 57, where the first primer has a first primer label, the second primer has a second primer label, the third primer has a third primer label, the second primer has a second primer label, at least a portion of one of the types of nucleotide triphosphates in the production of the first family of labeled, linear polynucleotide fragments is labeled with a first nucleotide label, at least a portion of one of the types of nucleotide triphosphates in the production of the second family of labeled, linear polynucleotide fragments is labeled with a second nucleotide label, the first terminator is labeled with a first terminator label, the second terminator is labeled with a second terminator label, the third terminator is labeled with a third terminator label and the fourth terminator is labeled with a fourth terminator label, and where the first primer label, the second primer label, the third primer label, the fourth primer label, the first nucleotide label, the second nucleotide label, the first terminator label, the second terminator label, the third terminator label and the fourth terminator label are all distinguishable from each other.

* * * * *

UNITED STATES PATENT AND TRADEMARK OFFICE
CERTIFICATE OF CORRECTION

PATENT NO. : 6,322,988 B1
DATED : November 27, 2001
INVENTOR(S) : Dawson et al.

It is certified that error appears in the above-identified patent and that said Letters Patent is hereby corrected as shown below:

Column 14,
Line 52, replace "by the either" with -- by either --

Signed and Sealed this

Twelfth Day of March, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,322,988 B1
DATED : November 27, 2001
INVENTOR(S) : Elliott P. Dawson and John A. Phillips, III It is certified that error appears in the above-identified patent and that said Letters Patent is hereby corrected as shown below:

Column 16,
Lines 25-26 and 29-30, replace "the first terminator or the second terminator" with -- the third terminator or the fourth terminator --.
Line 27, replace "the family of fragments" with -- the second family of fragments --.

Column 20,
Line 5, "first terminator and the second terminator" with -- the third terminator and the fourth terminator --.
Lines 7 and 10, replace "the family of fragments" with -- the second family of fragments --.
Line 8, replace "a first terminator or a second terminator" with -- a third terminator or a fourth terminator --.
Lines 13-14, replace "the first terminator or the second terminator" with -- the third terminator or the fourth terminator --.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,322,988 B1
DATED : November 27, 2001
INVENTOR(S) : Elliott P. Dawson and John A. Phillips, III It is certified that error appears in the above-identified patent and that said Letters Patent is hereby corrected as shown below:

Column 16,
Line 23, replace "the first terminator and the second terminator" with -- the third terminator and the fourth terminator --.
Line 25, replace "the family of fragments" with -- the second family of fragments --.
Line 30, replace "by the either" with -- by either --.

Column 20,
Line 12, replace "by the either" with -- by either --.

Signed and Sealed this

Fourteenth Day of December, 2004

JON W. DUDAS
*Director of the United States Patent and Trademark Office*